US006616277B1

(12) United States Patent
Davenport

(10) Patent No.: US 6,616,277 B1
(45) Date of Patent: Sep. 9, 2003

(54) SEQUENTIAL EYE SCREENING METHOD AND APPARATUS

(75) Inventor: Wayne E. Davenport, Huntsville, AL (US)

(73) Assignee: Vision Research Corporation, Birmingham, AL (US)

( * ) Notice: Subject to any disclaimer, the term of this patent is extended or adjusted under 35 U.S.C. 154(b) by 0 days.

(21) Appl. No.: 09/897,543

(22) Filed: Jul. 2, 2001

(51) Int. Cl.[7] .................................................. A61B 3/10
(52) U.S. Cl. ....................................... 351/221; 351/206
(58) Field of Search ................................ 351/201, 202, 351/205, 206, 221, 246; 600/558; 396/18

(56) References Cited

U.S. PATENT DOCUMENTS

| | | | |
|---|---|---|---|
| 3,806,725 A | 4/1974 | Leitz | 250/201 |
| 3,986,030 A | 10/1976 | Teltscher | 250/349 |
| 4,171,877 A | 10/1979 | Karasawa | 351/14 |
| 4,266,861 A | 5/1981 | Sawa | 351/7 |
| 4,305,398 A | 12/1981 | Sawa | 128/633 |
| 4,523,820 A * | 6/1985 | Kaakinen | 351/206 |
| 4,586,796 A | 5/1986 | Molteno | 351/206 |
| 4,669,836 A * | 6/1987 | Richardson et al. | 351/206 |
| 4,717,952 A | 1/1988 | Kohayakawa | 358/113 |
| 4,834,528 A * | 5/1989 | Howland et al. | 351/206 |
| 4,836,670 A | 6/1989 | Hutchinson | 351/210 |
| 4,950,069 A | 8/1990 | Hutchinson | 351/210 |
| 4,989,968 A | 2/1991 | Freedman | 351/206 |
| 5,157,427 A * | 10/1992 | Humphrey | 351/205 |
| 5,204,703 A | 4/1993 | Hutchinson | 351/210 |
| 5,218,387 A | 6/1993 | Ueno | 351/210 |
| 5,260,734 A | 11/1993 | Shindo | 354/219 |
| 5,280,313 A | 1/1994 | Kohayakawa | 351/211 |
| 5,355,895 A * | 10/1994 | Hay | 351/211 |
| 5,502,520 A * | 3/1996 | Cibis et al. | 351/200 |
| 5,530,493 A | 6/1996 | Suzuki | 351/206 |
| 5,543,865 A | 8/1996 | Nanjo | 351/206 |
| 5,632,282 A | 5/1997 | Hay | 128/745 |
| 5,668,621 A | 9/1997 | Nanjo | 351/206 |
| 5,684,561 A | 11/1997 | Yancy | 351/209 |
| 5,953,100 A | 9/1999 | Sarver et al. | 351/206 |
| 5,989,194 A | 11/1999 | Davenport | 600/558 |
| 6,027,216 A | 2/2000 | Guyton | 351/200 |
| 6,089,715 A * | 7/2000 | Hoover et al. | 351/221 |
| 6,090,051 A | 7/2000 | Marshall | 600/558 |
| 6,095,989 A | 8/2000 | Hay | 600/558 |

OTHER PUBLICATIONS

Simons, Kurt, PhD, Preschool Vision Screening: Rationale, Methodology and Outcome, Survey Of Ophthalmology, vol. 41, No. 1.

* cited by examiner

Primary Examiner—Marvin M. Lateef
Assistant Examiner—John R. Sanders
(74) Attorney, Agent, or Firm—Waddey & Patterson; Larry W. Brantley

(57) ABSTRACT

A method and apparatus for detecting diseases and abnormalities of a patient's eyes is disclosed. The apparatus includes an image-recording device for recording images of the patient's eyes while illuminated with infrared light and while at least two different meridians of the patient's eyes are illuminated with visible light in a time period shorter than the response time of the patient's eyes. The apparatus further includes a light source for illuminating the patient's eyes with infrared and two different meridians of the patient's eyes with visible light, and a control system for controlling the image-recording device and the light source. In one embodiment, the image-recording device includes a high-speed digital camera, the light source includes a group of infrared light-emitting diodes (LEDs) and a pair of flashes, and the control system is a computer system. The invention is useful in detecting both refractive and non-refractive errors of the eyes.

40 Claims, 13 Drawing Sheets

-1 Diopter　　　Flash #1　　　　　　　　Flash #2

-5 Diopter　　　Flash #1　　　　　　　　Flash #2

+1 Diopter　　　Flash #1　　　　　　　　Flash #2

+5 Diopter　　　Flash #1　　　　　　　　Flash #2

Astig. Vert Axis    Flash #1                    Flash #2

Astig. Horz. Axis   Flash #1                    Flash #2

Normal Eyes

Exotropia

First Order Approximation:

$\alpha = \tan^{-1}(x/y)$, y (nominally)=12.5mm

SEQUENTIAL EYE SCREENING METHOD AND APPARATUS

TECHNICAL FIELD

The present invention relates generally to a method and apparatus for screening a patient to detect diseases and abnormalities of the eyes and lids.

More particularly, this invention pertains to a method and apparatus for generating a pair of images of the eyes in a time period that is shorter than the pupillary response time of the eye and analyzing these images to detect diseases and other abnormalities.

BACKGROUND OF THE INVENTION

It is well known that approximately 2–5% of children will develop some degree of amblyopia and another 15%–20% possess some form of visual malady. Screening eyes to detect diseases and abnormalities, such as refractive errors, both spherical and cylindrical in optical power, ocular alignment, media opacities, and ptosis, is very important because if these diseases are not corrected before the ages of 7 to 9, a person may suffer irreversible vision loss. Screening eyes in young children accurately and consistently, however, is not an easy task, especially when computer automated diagnosis in involved.

As mentioned previously, many of these diseases and abnormalities must be detected and corrected at an early age, and, accordingly, the typical screening patient is a child in preschool through third grade. Generally, patients in this age group have a very short attention span, which makes it difficult to perform an accurate screening of the eye. As a result, screening tests for patients in this age group must be expeditious, simple, passive (i.e., no patient-technician interaction), non-intrusive, and portable enough for field-testing in the school environment. One type of screening test that satisfies these criteria is photoscreening.

Photoscreening is the process of taking a photograph of the patient's eyes and analyzing that photograph to detect diseases and other abnormalities. In general, photoscreening systems include a camera (film or digital), and single, multiple, or ring-type flashes located near (or on) the camera's optical axis. By simultaneously illuminating the eyes with the flash and taking a photograph, one creates an image that may be analyzed to detect diseases and other abnormalities in the eyes.

It is known in the art that Caucasians produce a distinctive red retinal reflex, or retinal return reflection in a photo-screened image. This red retinal reflection is visible to the camera when illuminated by a near (or on) axis flash and the pupils are sufficiently dilated. Other ethnic groups, however, differ rather dramatically. Persons from African-American, Asian, and Hispanic descent do not, in general, produce a red retinal reflex and, in fact, with an eye that can focus properly, off axis photoscreening may produce no detectable retinal reflex. This is particularly alarming since it may be difficult, if not impossible, to detect cataracts or other media opacities in these ethnic groups via traditional photoscreening techniques. The present invention overcomes the deficiencies associated with traditional photoscreening and allows a robust method for computer-aided screening.

For example, U.S. Pat. No. 5,989,194 issued to Davenport et al. on Nov. 23, 1999 and entitled, "Method and Apparatus for Detecting Ocular Disease and Abnormalities" and U.S. Pat. No. 6,095,989 issued to Hay et al. on Aug. 1, 2000 and entitled, "Optical recognition methods for locating eyes" (continuation-in-part of U.S. Pat. Nos. 5,632,282 and 5,355,895.) both teach a screening system which includes a singular flash and provides information in only one meridian of the eye. As a result, these systems are unable to detect astigmatism in some axes of the eye and, in addition, neither of these patents allows one to obtain quantitative numbers relating to the patient's pupil size or baseline retinal reflectivity prior to the actual photoscreening process. It should also be noted that the Hay patent includes extensive techniques for computer analysis of typical photoscreened images and, therefore, has inherent difficulties analyzing these images on the minority groups mentioned earlier. The contention is that robust analysis of traditional (single, double, or ring type off-axis flash systems) photoscreened images for media opacities and refractive errors is difficult to perform, and is especially difficult to analyze via computer image processing. The present invention, with its novel infrared prescreening capabilities and sequentially captured, multi flash system, allows for robust image analyses across all ethnic groups by both manual and digital means.

A two-flash screening system is described in U.S. Pat. No. 4,523,820 issued to Kaakinen on Jun. 18, 1985, and entitled "Procedure and Means for Establishing and Recording Errors of the Eye". The '820 patent teaches a system and method for obtaining a photograph of a patient's eyes by simultaneously triggering two flashes located in different meridians of the eye. It is true that this system is more robust in the detection of astigmatism over single flash systems, but, because both flashes are triggered simultaneously and overlap in the resulting photograph, it is difficult to interpret the contributions made from each flash. While it may be possible to determine that a patient's vision has sphere and cylinder errors, the overlapped images make it difficult to specify the extent of these errors. This system also suffers from problems associated with traditional photoscreening systems mentioned earlier.

Additional two-flash photoscreening systems are described in U.S. Pat. No. 4,989,968 issued to Friedman on Feb. 5, 1991 and entitled, "Photocreening Camera System" and U.S. Pat. No. 6,089,715 issued to Hoover et al. on Jul. 18, 2000 and entitled "Automated Photo refractive Screening". Both of these patents describe systems that are similar to the ones in the '820 patent, except that the flashes are either mechanically rotated or the camera is physically rotated in order to get two singular photographs, each containing information regarding different meridians of the eye. The primary problem with both of these systems is the 15 to 20 second time delay between the flashes. During this time delay, the patient's pupils may change in diameter, the eyes may change in accommodation, or the eyes may align differently, any of which will cause a significant increase in false positive screenings. Again, both of these systems suffer from problems associated with traditional photoscreening systems mentioned earlier. It should be noted that the algorithms employed by the Hoover patent base their pupil detection on the red retinal reflex (step 52 '715 patent) in order to perform computer-aided diagnosis.

Finally, a screening system utilizing a ring flash is disclosed in U.S. Pat. No. 4,586,796 issued to Molteno on May 6, 1986 and entitled, "Testing to Determine the Fixation and Focusing of Living Eyes". While this system does allow one to determine that there is a problem with the eyes, determining the type of problem is difficult, This is true because the ring flash is symmetrical around the optical axis and, as a result, while it is possible to detect both cylindrical and spherical optical errors, it is unclear in the photograph whether the spherical error is myopic or hyperopic in nature or in which axis the cylinder power is oriented.

Thus, what is needed is a robust system and method for screening eyes that allows one to detect and identify various types of diseases and abnormalities in the eyes with a high degree of accuracy and specificity across all ethnic groups.

SUMMARY OF THE INVENTION

The present invention provides a method and apparatus for detecting diseases and abnormalities of the eyes by generating a pair of images of the patient's eyes in a time period that is shorter than the pupillary response time of the patient's eyes. The apparatus includes a device for recording images of a patient's eyes while 1) the eyes are being illuminated with infrared light, and 2) the eyes are being sequentially illuminated with visible light in at least two different meridians of the eyes in a time period that is shorter than the pupillary response time of the eyes. The apparatus also includes a light source for 1) illuminating the patient's eyes with infrared light, and 2) sequentially illuminating the patient's eyes in a time period that is shorter than the pupillary response time of the patient's eyes. Finally, the apparatus includes a system for controlling both the image-recording device and the light source.

The method includes the steps of illuminating and recording images of the patient's eyes with infrared light. These infrared images are used to determine the pupil size and baseline retinal reflectivity of the patient's eyes as well as to identify non-refractive errors, such as cataracts, exotropia, and esotropia. These steps are followed by the sequential triggering of a visible light source in at least two different meridians of the patient's eyes in a time period shorter than the patient's pupillary response time and capturing images of the patient's eyes while each meridian is illuminated. These visible light images are used to identify refractive errors, such as astigmatism, myopia, and hyperopia. In addition, by capturing the images faster than the pupillary response time of the patient's eyes, the present invention eliminates errors caused by changes in dilation, focusing, or alignment.

In one embodiment, the image-recording device includes a high-speed digital color camera, the light source includes a plurality of infrared light-emitting diodes (LEDs) and a pair of flashes commonly used with consumer cameras, and the control system includes a computer. In this embodiment, the high-speed digital camera, which normally includes an infrared cut-off filter covering a sensor, is made sensitive to infrared light by simply removing the filter. As a result, the camera is sensitive to both visible and infrared light. It is impractical, however, to capture an image when the patient's eyes are illuminated by both infrared and visible light because this would degrade the color balance of the visible picture as well as over-write the visible and infrared images. Therefore, this embodiment captures images while there is either 1) infrared illumination or 2) visible illumination. In an effort to preserve color balance while acquiring the visible pictures, the flashes are outfitted with the same infrared cut-off filters that were used on the sensor thereby prohibiting any infrared light generated by the visible flashes from reaching the camera's sensor. The computer controls the camera, the visible flashes and, using a software program, analyzes the infrared and visible light images of the patient's eyes to determine pupil size, baseline retinal reflectivity, non-refractive errors, and refractive errors.

DESCRIPTION OF THE PREFERRED EMBODIMENTS

Figure 1:
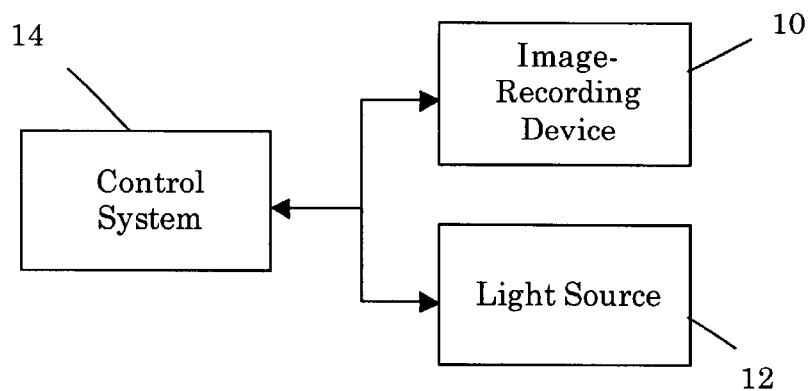
FIG. 1 is a block diagram of one embodiment of the present invention.

Referring to FIG. 1, the present invention includes an image-recording device 10, a light source 12, and a control system 14. The image-recording device 10 is operable to record images of a patient's eyes while illuminated by infrared light and while sequentially illuminated by visible light in a time period that is shorter than the pupillary response time of the patient's eyes. The response time of a patient's pupils in this context is defined as the time required by a patient's pupils to respond to external stimuli, such as the time required for a patient's pupils to respond to a flash of light generated by a camera flash.

The light source 12 is operable to illuminate the patient's eyes with infrared light and to sequentially illuminate two different meridians of the patient's eyes in a time period shorter than the pupillary response time of the patient's eyes. While the discussion of the present invention that follows refers to a system that illuminates two different meridians of the patient's eyes, alternative embodiments might illuminiate more than two meridians. In other words, the light source 12 in alternative embodiments might sequentially illuminate more than two different meridians of the patient's eyes in a time period shorter than the pupillary response time of the patient's eyes.

The control system 14 is in communication with and controls both the image-recording device 10 and the light source 12. Specifically, the control system 14 is operable to cause the image-recording device 10 to record images of the patient's eyes and to cause the light source 12 to generate infrared light and visible light in two different meridians of the patient's eyes in a time period smaller than the response time of the patient's eyes. In addition, the control system 14 analyzes the infrared and visible light images to determine pupil size, non-refractive errors, and refractive errors.

Figure 2:
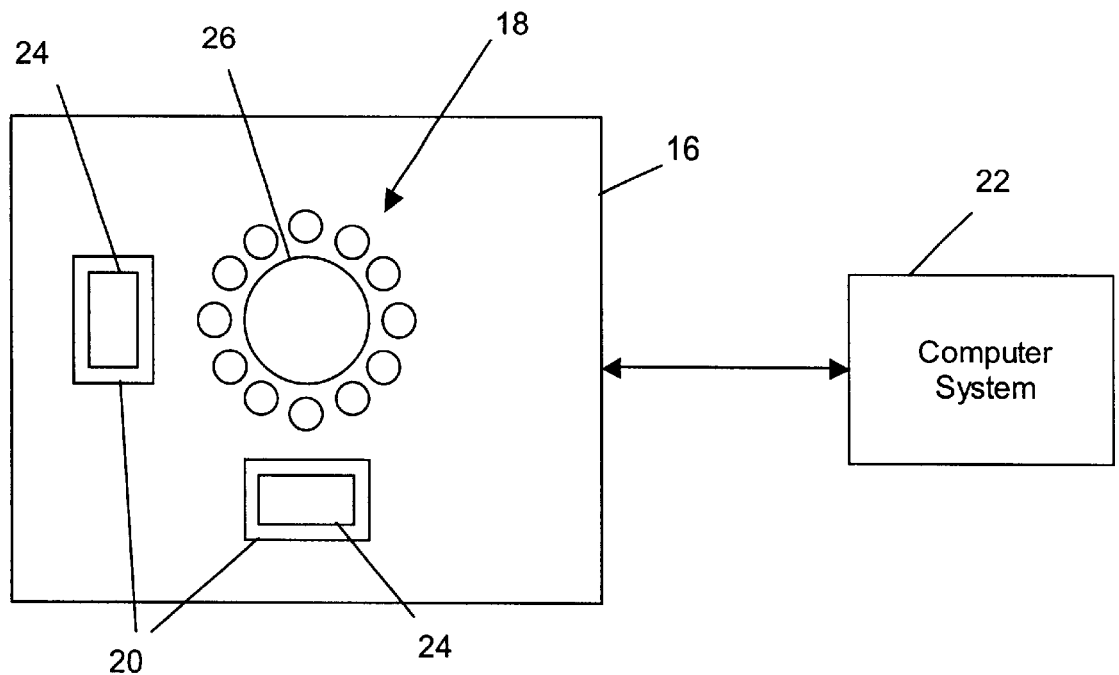
FIG. 2 is a block diagram of a second embodiment of the present invention.
Figure 3:
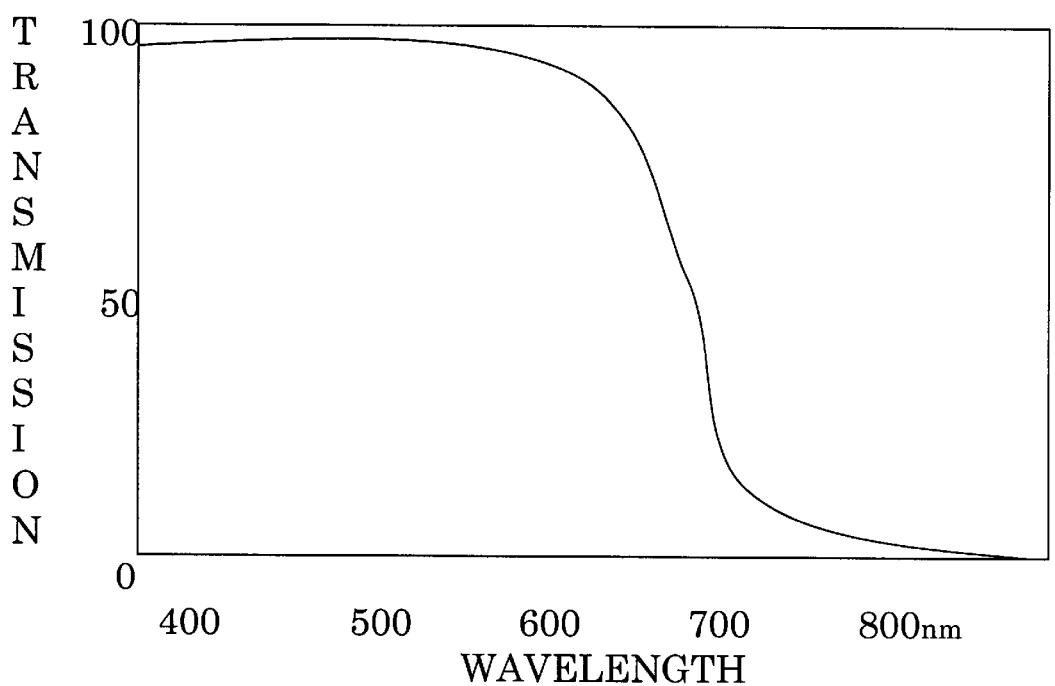
FIG. 3 is a plot showing the filter characteristics of the filter used with each flash shown in FIG. 2.

Referring to FIG. 2, in one embodiment of the present invention the image-recording device 10 includes a high-speed, digital, color, camera 16, the light source 12 includes a plurality of infrared light-emitting diodes (LEDs) 18 and a pair of flashes 20 that are connected to the camera 16, and the control system 14 includes a computer system 22 including a monitor (not shown) for displaying both infrared and visible images of the patient's eyes, which is connected to the camera 16, the LEDs 18, and the pair of flashes 20. In addition, the infrared filter (not shown) built into the camera 16 is removed and flashes 20 include infrared filters 24 for filtering any infrared light generated by the flashes 20. The filter characteristics of the filters 24 are shown in FIG. 3.

Figure 4:
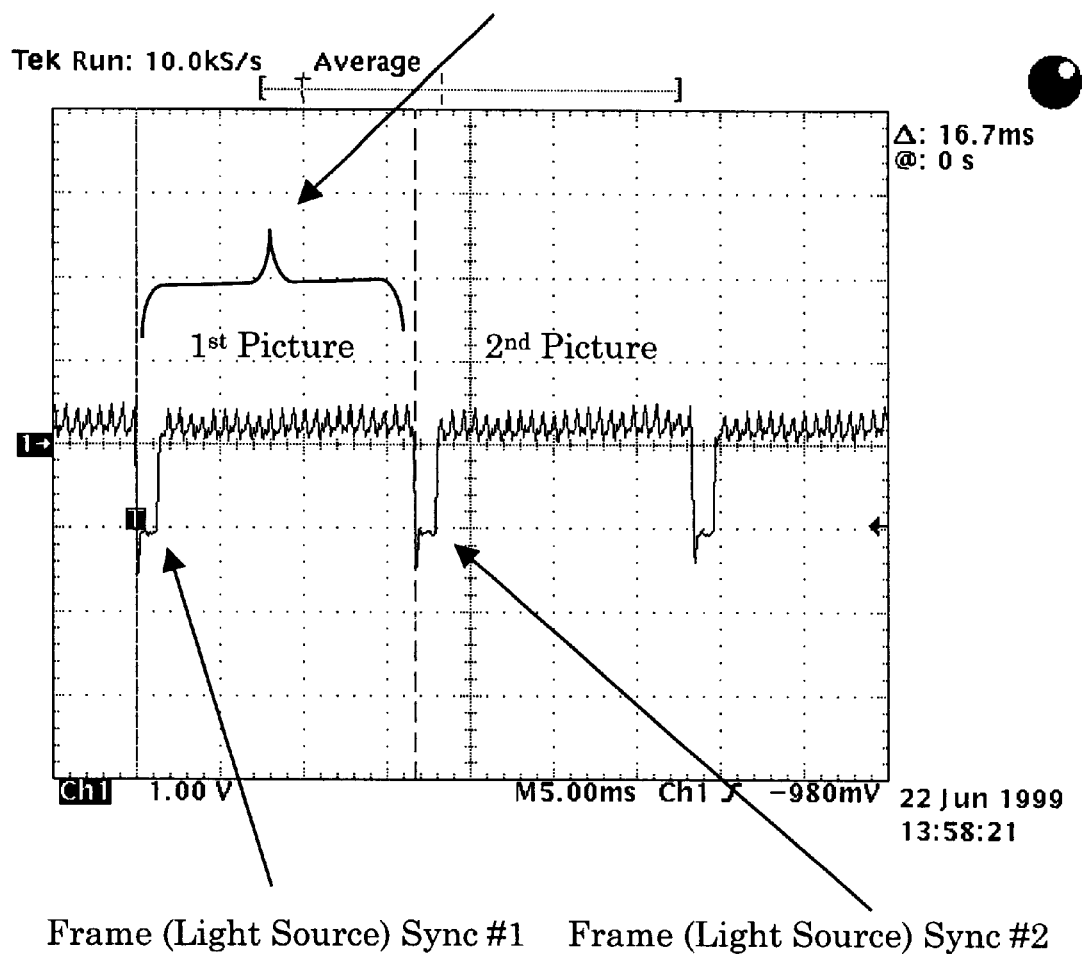
FIG. 4 is a plot of an output signal from the digital camera shown in FIG. 2 that is used to control the sequential triggering of the flashes.

In this embodiment, the high-speed, digital, color, camera 16 is a Vitana PL-A634 Color CMOS camera with 1280× 1024 (programmable) resolution and includes horizontal, vertical, and strobe output syncs (not shown) and the flashes 20 are triggered based on the strobe output sync of the camera 16, which is shown in FIG. 4.

The LEDs 18 are manufactured by Photonic Detectors (part no. PDI-E803), the flashes 20 are Vivitar model 283 flashes, and the infrared filters are Schott kg-3 filters. Finally, the computer 22 is a Dell Pentium 3 computer system using an Intel Pentium 3 processor.

The camera 16 includes a conventional photographic objective lens 26 (see FIG. 2) that is designed to focus light having wavelengths ranging from approximately 400 nanometers to 650 nanometers. In alternative embodiments, the objective lens 26 may be a custom designed lens that is specially coated and optimized for focusing light having wavelengths ranging from 500 nanometers to 950 nanometers. The objective lens 26 and shutter speed of the camera 16 must be adjusted when capturing images of the patient's eyes using infrared light and visible light. The adjustment to the objective lens 26 may be performed manually or using an adjustment mechanism (not shown), such as a stepper motor.

The adjustment to the camera's shutter speed may be controlled by the control system 14. In one embodiment, the shutter speed is set to $1/30^{th}$ of a second for recording infrared images and $1/500^{th}$ of a second for recording the visible light images. The shutter speed of $1/500^{th}$ of a second is approximately the flash duration time and is used to ensure underexposure of the infrared light (i.e., the exposure is not long enough for the infrared light to register on the visible light image). This is desirable because infrared light is not wanted in the exposure since the visible light image is to be used for refractive error determination.

In another embodiment, the present invention includes several small flashing LEDs (not shown) placed near the camera's objective lens 26 to get the attention of the patient and to allow the patient to focus his/her eyes at the proper distance for accurate refractive screening. Although this embodiment uses flashing LEDs, other types of devices may also be included in the present invention to get the attention of the patient.

Although the present invention is described in FIG. 2 as having a light source 12 that includes an infrared light source, such as infrared LEDs 18, the inventor of the present invention also contemplates a system that does not include the LEDs 18. In such an embodiment, the infrared filter (not shown) of camera 16 does not have to be removed and the flashes 20 do not include infrared filters 24.

Figure 5:
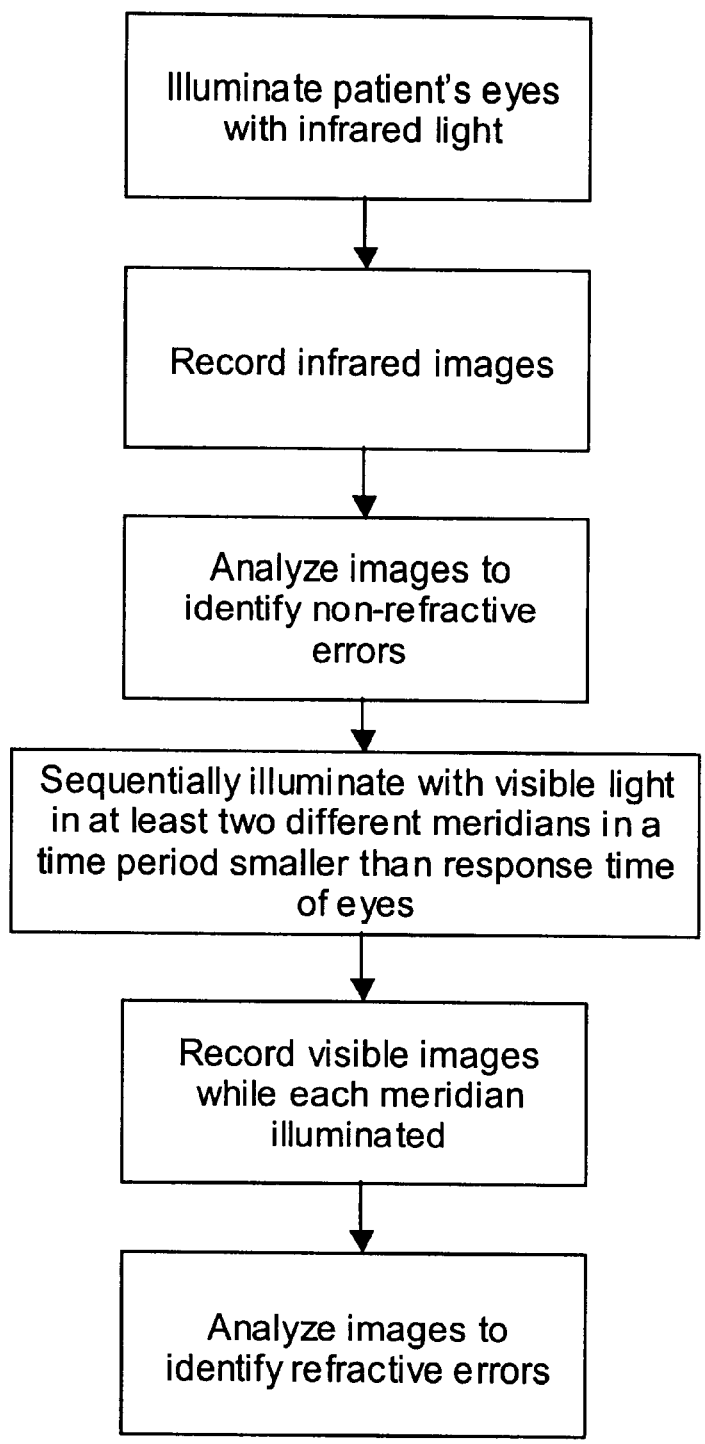
FIG. 5 is a flowchart of the method steps included in the present invention.
Figure 6:
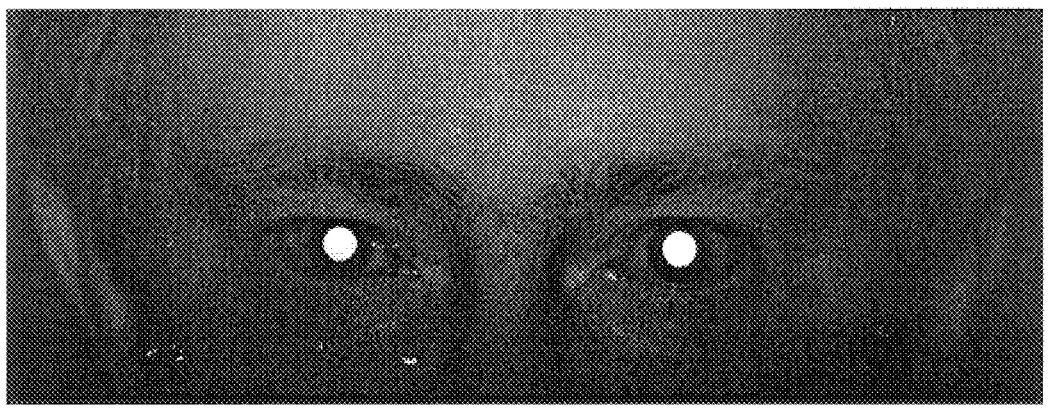
FIG. 6 is a picture showing a patient's face and eyes illuminated using the infrared light emitting diodes.

Referring to FIG. 5, the method disclosed in the present invention includes the steps of illuminating the patient's eyes with infrared light using the light source 12, recording images of the patient's eyes while illuminated with infrared light, and analyzing the resulting infrared images to identify non-refractive errors, such as cataracts and strabismus. A typical resulting infrared image is shown in FIG. 6.

Cataracts may be identified by reviewing an infrared image of the patient's eyes and identifying dark spots in the image of the eyes. Note that the image of the eyes shown in FIG. 6 does not include any dark spots and accordingly, this patient did not have cataracts at the time the image was recorded.

Figure 7:
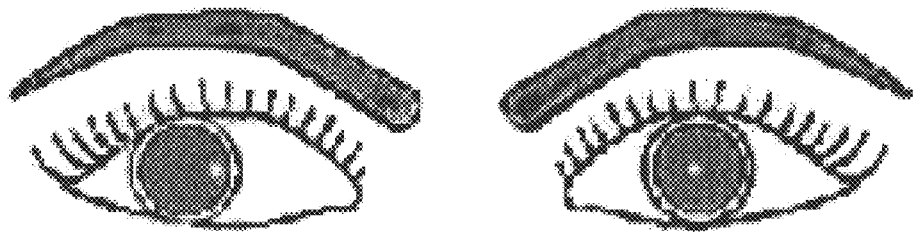
FIG. 7 is a drawing showing a patient's eyes illuminated with infrared light and indicating esotropia.
Figure 8:
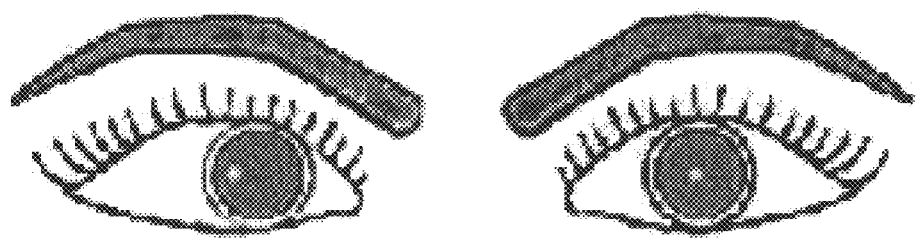
FIG. 8 is a drawing showing a patient's eyes illuminated with infrared light and indicating exotropia.

Strabismus, i.e., exotropia (eye turned toward temple) and esotropia (eye turned toward nose), may also be detected by reviewing the infrared images of a patient's eyes. Specifically, strabismus may be detected by reviewing the infrared image and calculating the gaze angle of the eyes by locating the reflection of the light source 12 off of the cornea (the outer surface of the eye) and comparing that to the centroid of the pupil. As shown in FIG. 6, this reflection appears as a bright spot in the image near the center of the patient's eyes. FIGS. 7 and 8 show an image of a patient's eyes indicating exotropia and esotropia, respectively.

Note that the visible light images, which will be discussed in further detail below, may also be used to detect exotropia and esotropi because these images also contain corneal reflections generated by the visible light flashes. Recall, however, that with the invention disclosed in the '820 patent, two flashes are triggered simultaneously and, as a result, a pair of corneal reflections are created in the resulting images that makes it difficult to examine the area of the patient's eyes under the reflections. Since the present invention uses two sequentially triggered visible light flashes, the resulting visible light images only contain one corneal reflection and, accordingly, less area of the patient's eyes is obscured by the reflection.

Finally, the infrared images may also be used to determine pupil size, which is important in photoscreening. If the eyes are not dilated sufficiently, in most cases at least approximately 5 millimeters, then an insufficient amount of light enters the patient's eyes and it is difficult to screen the eyes properly. In addition, optical properties of a patient's eyes may cause the eyes to appear to have adequate focusing properties if the pupils are not dilated above 3–4 mm when, in fact, the eyes do not have adequate focusing properties.

In any event, the analysis to detect cataracts, strabismus, baseline retinal reflectivity, and pupil size may be performed manually (by a person reviewing the infrared images of the patient's eyes) or by using a computer. In one embodiment of the present invention, the computer 22 is operable to analyze the infrared images to determine these conditions. In this embodiment, the computer system 22 analyzes the infrared images by performing the steps shown in FIG. 15.

Figure 15:
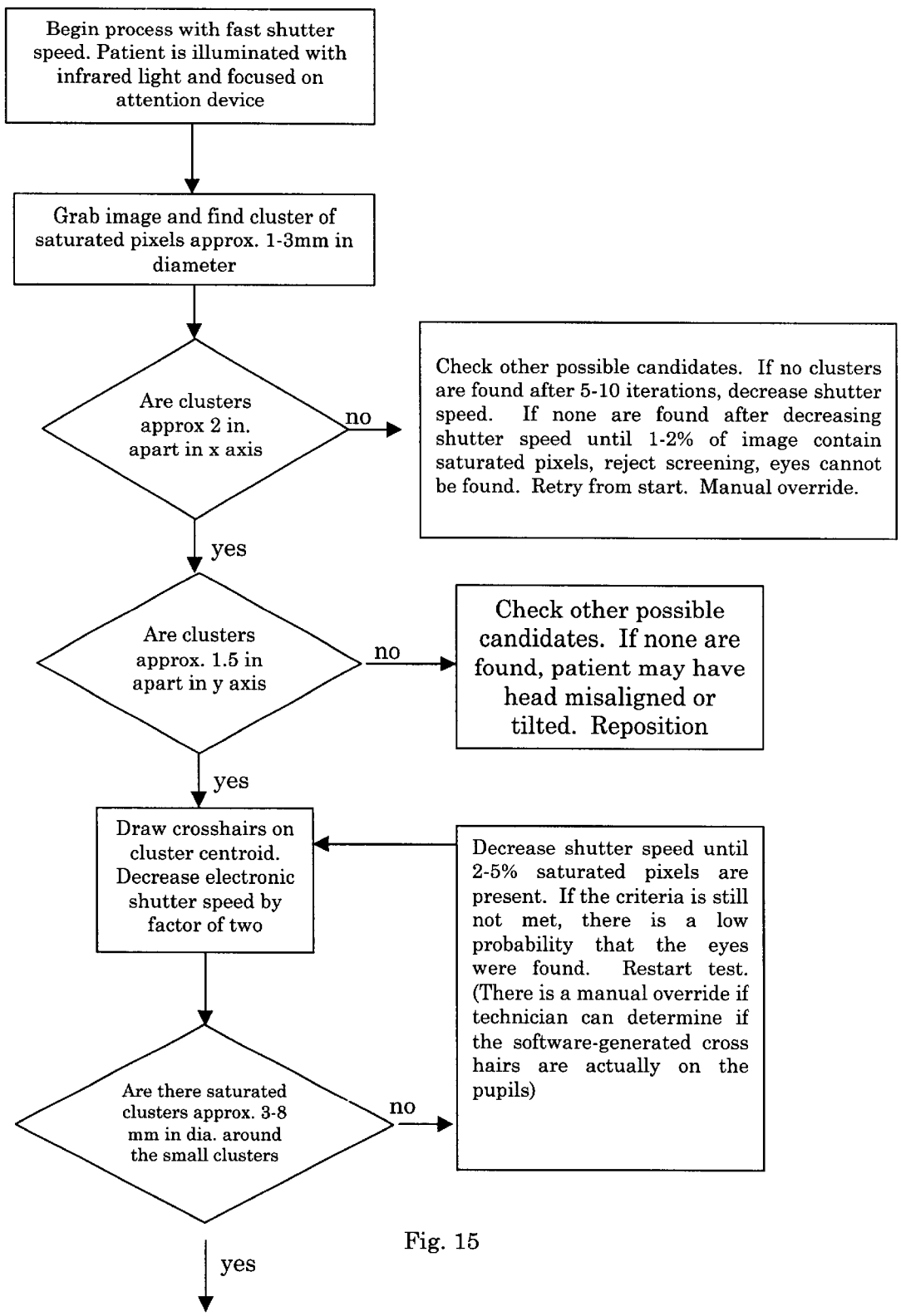
FIG. 15 is a flow chart showing the steps performed by the computer system to analyze infrared and visible light images of a patient's eyes.
Figure 15:
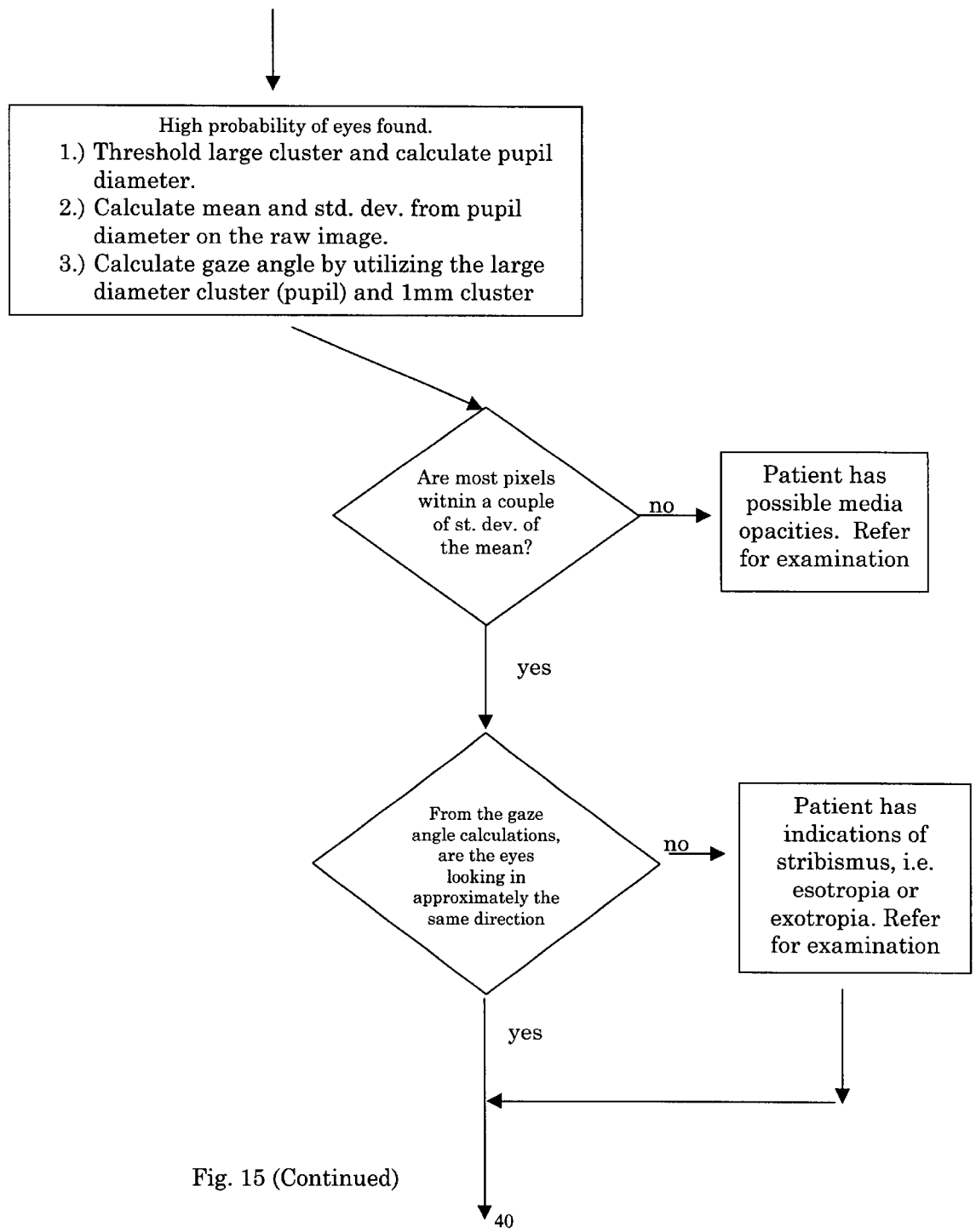
Figure 15:
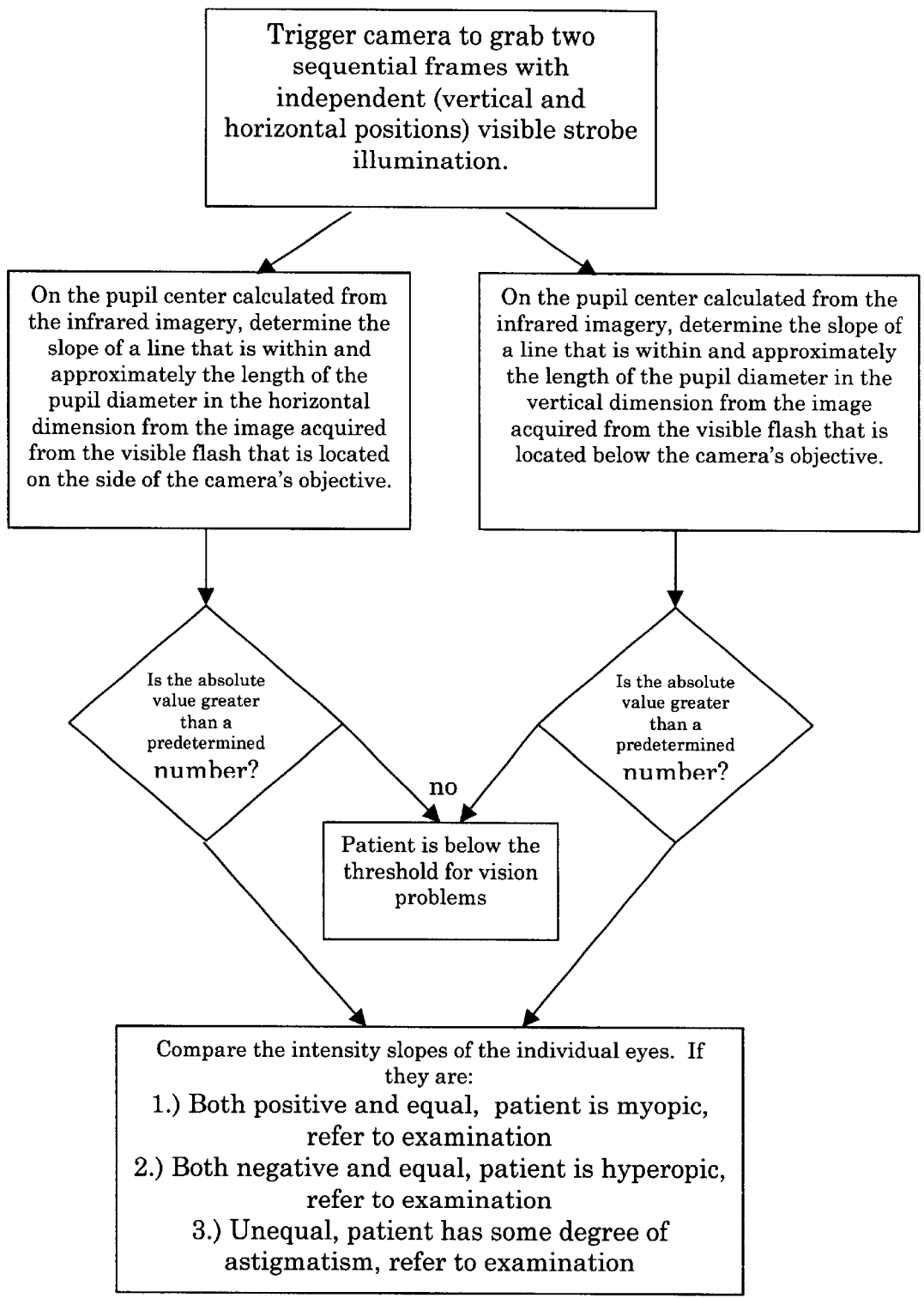

Referring to FIG. 15, the computer system 22 finds the patient's eyes in the infrared image. This is accomplished by searching the infrared images for first surface reflections, which typically will include a 3–4 saturated pixel cluster approximately 1 mm in diameter. Once the saturated pixels are located the computer system 22 determines if two sets of saturated pixels are separated by approximately 2 inches along the x-axis and approximately 1.5 inches along the y-axis. If the two sets are not separated by approximately 2 inches, the computer system 22 searches for additional sets of saturated pixels. If no additional sets are found after 5–10 iterations, the computer system 22 decreases the shutter speed in order to locate additional sets of saturated pixels. If the shutter speed is decreased to the point that a couple of $100^{th}$s of a percent of the image contains saturated pixels and the above criteria is not satisfied, the computer system 22 determines that the eyes cannot be found. At this point, a technician operating the computer system 22 can manually override the computer system 22 and proceed to the next step.

The pixels found that fit the above x-axis criteria are then subjected to tests to determine if they are aligned along the y-axis. If a pair of the candidate pixels are located within approximately 1.5 inches of each other along the y-axis, then the criteria is assumed met and the screening process continues. However, if none are found, the computer system 22 does not continue the screening of the infrared image and provides an indication to a technician operating the computer system 22 that there is not a high level of confidence that the patient's eyes have been found. In this case, the patient may have his/her head misaligned or tilted, the technician can reposition the patient, and the technician can restart the search process. In addition, the technician can manually override the computer system 22 and proceed to the next step.

Next, the computer system 22 determines if the pair of first surface reflections is surrounded by a "circle" or "cluster" (which is most likely the pupil of the eye) of approximately 10 to 50 illuminated pixels approximately 3–8 mm in diameter. To do this, the computer system 22 draws crosshairs on the pair of saturated pixels deemed to be the corneal reflex and decreases the shutter speed by approximately a factor of two and searches the resulting image for the "circles." If the "circles" are not found, the computer system 22 decreases the shutter speed until approximately 2–5% of the infrared image contains saturated pixels. If the "circles" still cannot be found, the computer system 22 determines that the eyes were not found and restarts the search process. A technician can override the computer system 22 and proceed to the next step since he or she can determine that the crosshairs are actually positioned on the patient's pupils.

Next, the computer system 22 calculates the pupil diameter using the "circles" by thresholding the image. If the patient's eyes are not dilated 5 millimeters or more, the computer system 22 provides an indication of that fact to the operator of the present invention. The amount of eye dilation determines the confidence level that is attached to conlcusions drawn by analyzing the infrared images. For example, if the patient's eyes are dilated less than 5 mm, then the confidence level associated with the refractive error screening is low. This is true primarily because when the patient's eyes are dilated less than 5 mm it is possible to appear to have proper focus when, in reality, the eyes do not. This is due to: 1) the decreased amount of light entering the eye and 2) optical systems have better depth of focus with smaller apertures. Therefore, screening with pupils dilated less than 5 mm will result in an increase in the occurrence of false negatives.

Next, the computer system 22 looks for media opacities, such as cataracts, by measuring the intensity of the light of the infrared image of the patient's eyes. This is accomplished by calculating the illumination mean and standard deviation of the "circle" area referenced above using the raw infrared image. If an area of the patient's pupils includes low intensity levels or the pupillary region has a high standard deviation, the computer system 22 determines that media opacities, such as cataracts, may be present in the patient's eyes and provides an indication of that fact to the technician.

Finally, the computer system 22 determines the gaze angle of the patient's eyes, and, in turn, if the patient has symptoms of esotropia or exotropia. This is accomplished by calculating the distance between the corneal reflection and the geometrical center of each pupil. To illustrate, consider FIG. 17.

Figure 17:
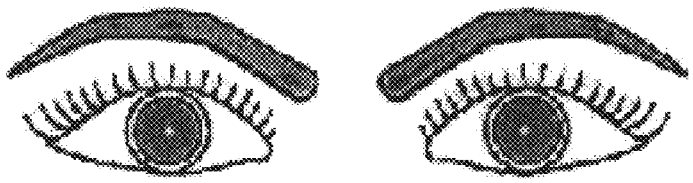
FIG. 17 is a drawing showing a front view and top view of a patient with exotropia.
Figure 17:
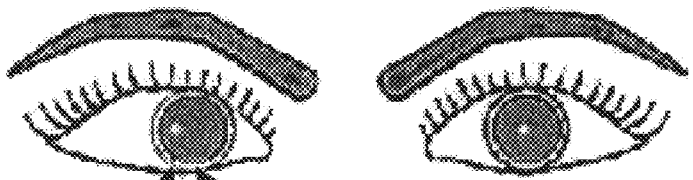
Figure 17:
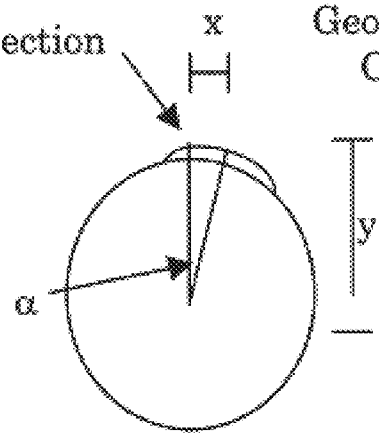
Figure 17:
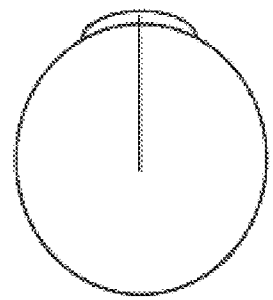

FIG. 17 includes a front view and a top view of a pairs of eyes having esotropia, the right eye being aligned correctly and the left eye being misaligned. The front views include white dots in the pupil labeled "corneal reflection" and cross hair center points labeled "pupil geometrical center." The top view also includes points that correspond to the location of the corneal reflections and the geometric centers, and are labeled accordingly.

Referring to the right top view, the corneal reflection point and the cross hair center point are located appoximately at the same position, indicating that the eye is aligned correctly. In the left top view, however, the corneal reflection point and the cross hair center point are not located in approximately the same position and this indicates that the eye is misaligned. The computer system 22 calculates the distance between the corneal reflection point and the cross hair center point and expresses this distance as an angle, $\alpha$. This angle $\alpha$ is referred to as the gaze angle of the eyes and is used to determine if the eyes are misaligned. If the gaze angle is approximately zero, then a patient does not have an alignment problem. If, on the other hand, the gaze angle is non-zero, then the patient has symptoms of an alignment problem.

In one embodiment, the gaze angle, $\alpha$, is calculated using the distance between the corneal reflection and the cross hair center point of each eye, labeled as the x distance, and the distance between the center of the eye and the cross hair center point, labeled as the y distance (this distance is usually approximately 12.5 mm, but it may vary from person to person). A first order approximation of the gaze angle is then calculated by taking the inverse tangent of the ratio of the x distance over the y distance. In other embodiments, however, other types of approximations may be used as well.

Returning to FIG. 5, the method disclosed in the present invention further includes the steps of sequentially illuminating two different meridians of the patient's eyes in a time period that is shorter than the pupillary response time of the patient's eyes, recording images of the patient's eyes while each meridian is illuminated, and analyzing the resulting visible images to identify refractive errors in the patient's eyes. FIGS. 9–14 show the types of images that typically result from this process.

Figure 9:
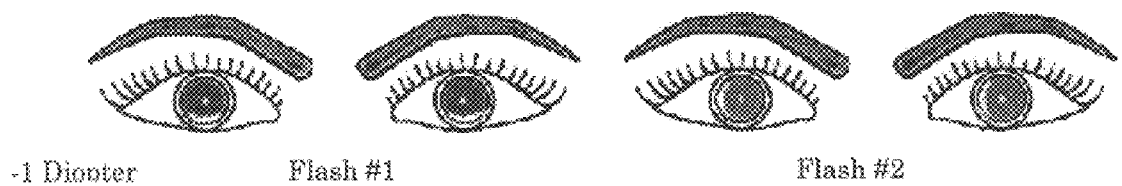
FIG. 9 is a figure showing a pair of images of a patient's eyes indicating −1.0 diopeters of myopia (nearsightedness).
Figure 10:
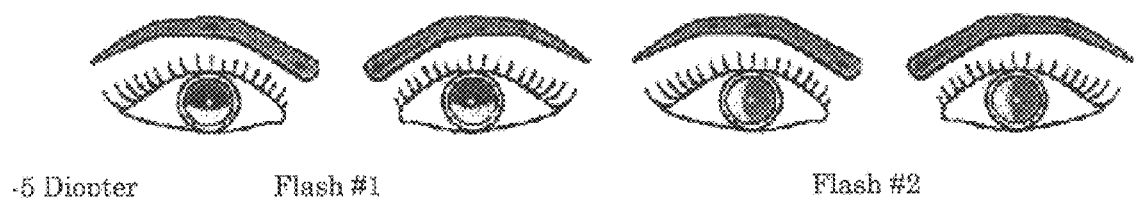
FIG. 10 is a figure showing a pair of images of a patient's eyes indicating −5.0 diopeters of myopia

FIGS. 9 and 10 show a patient's eyes indicating approximately −1.0 diopters of myopia (nearsightedness) and approximately −5.0 diopters of myopia, respectively. Note that the crescents shown in FIG. 10 are much higher in the −5.0 diopter patient as compared to the −1.0 diopter patient. The appearance of the crescents in the images of the patient's eyes is caused by defocusing of the light source 12 on the retina of the patient's eyes and the more defocusing (i.e., the worse the vision), the higher the crescent.

Figure 11:
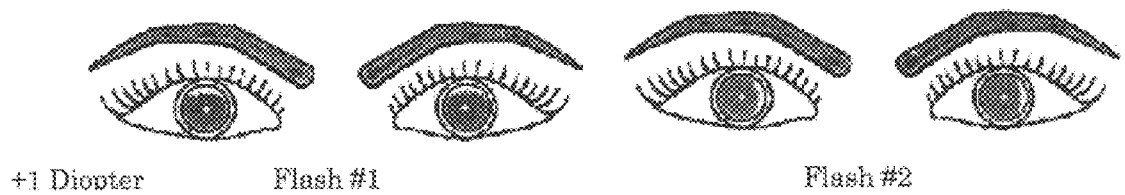
FIG. 11 is figure showing a pair of images of a patient's eyes indicating +1.0 diopeters of hyperopia (farsightedness).
Figure 12:
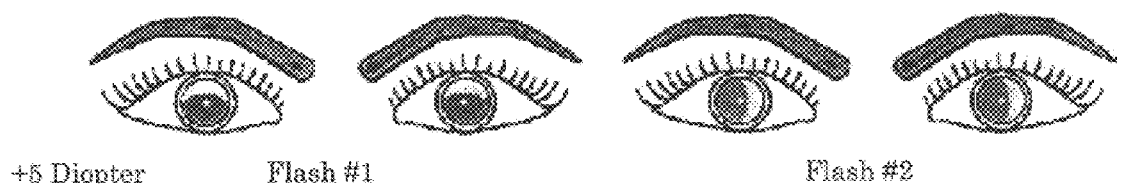
FIG. 12 is a figure showing a pair of images of a patient's eyes indicating +5.0 diopeters of hyperopia.

FIGS. 11 and 12 show a patient's eyes indicating approximately +1.0 diopters and +5.0 diopters of hyperopia (farsightedness). Note that these images are similar to the images shown in FIGS. 9 and 10 except that the crescents appear on the opposite side of the patient's eyes.

Figure 13:
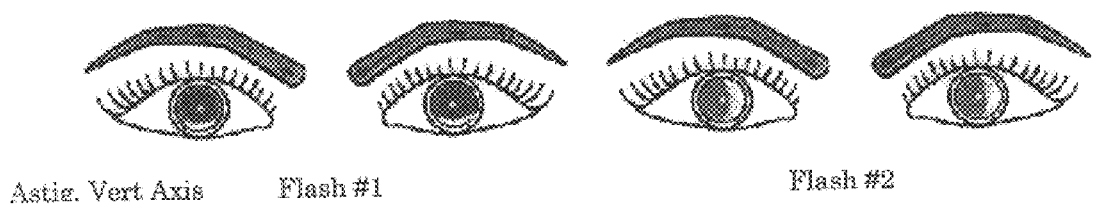
FIG. 13 is a drawing showing a patient's eyes indicating astigmatism (cylinder optical power oriented vertically).
Figure 14:
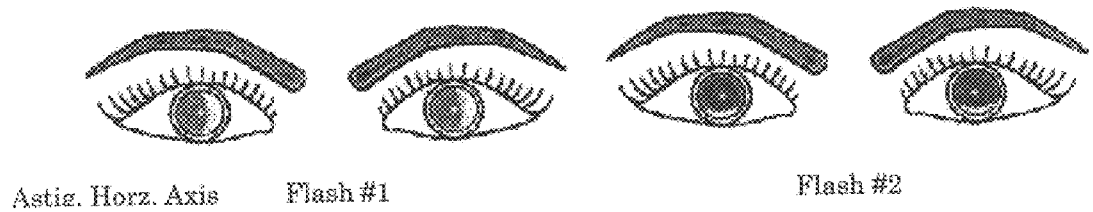
FIG. 14 is a drawing showing a patient's eyes indicating astigmatism (cylinder optical power oriented horizontally).

Finally, FIGS. 13 and 14 show a patient's eyes indicating approximately −1.0 diopters of astigmatism (cylinder optical power) oriented vertically and approximately −1.0 diopters of astigmatism oriented horizontally, respectively.

As was the case with the analysis to detect cataracts, strabismus, and pupil size, the analysis to detect refractive errors may be performed manually (by a person reviewing the infrared images of the patient's eyes) or by using a computer. In one embodiment of the present invention, the computer 22 is operable to analyze the visible light images to determine these conditions. In this embodiment, the computer system 22 analyzes the visible light images by performing the following steps.

Referring again to FIG. 15, the computer system 22, using the pupil center calculated using the infrared image, defines a line along the center of the pupil in the first visible light image (i.e., the image obtained using the flash located on the side of the camera's objective lens) that is approximately 5 pixels wide and equal in length to the horizontal diameter of the pupil calculated using the infrared image of the eye. Next, the computer system 22 calculates the degree of slope in this line.

The computer system 22 then defines a line along the center of the pupil in the second visible light image (i.e., the image obtained using the flash located below the camera's objective lens) that is approximately 5 pixels wide and equal in length to the vertical diameter of the pupil calculated using the infrared image of the eye. The computer system 22 then calculates the degree of slope in this line.

In both cases, the degree of slope is calculated by comparing the intensity of pixels in the line. If the pixels are all equally illuminated, then the slope of the line is zero. If, on the other hand, the pixels have different amounts of illumination, then the slope is non-zero, i.e., either positive or negative. In addition, if the absolute value of the slop is below a predetermined threshold value, then the computer system 22 determines that the patient does not have any refractive errors.

Finally, the computer system 22 compares the intensity and degree of slope in each image to to determine if a patient is myopic, hyperopic, or has some degree of astigmatism. If the slopes are both positive and equal, then the computer system 22 determines that the patient is myopic. If, on the other hand, the slopes are both negative and equal, then the computer system 22 determines that the patient is hyperoptic. If the slopes are unequal, the computer system 22 determines that the patient has some degree of astigmatism. The degree of astigmatism is determined by the ratio of the two slopes; the higher the ratio, the higher the degree of astigmatism.

Figure 16:
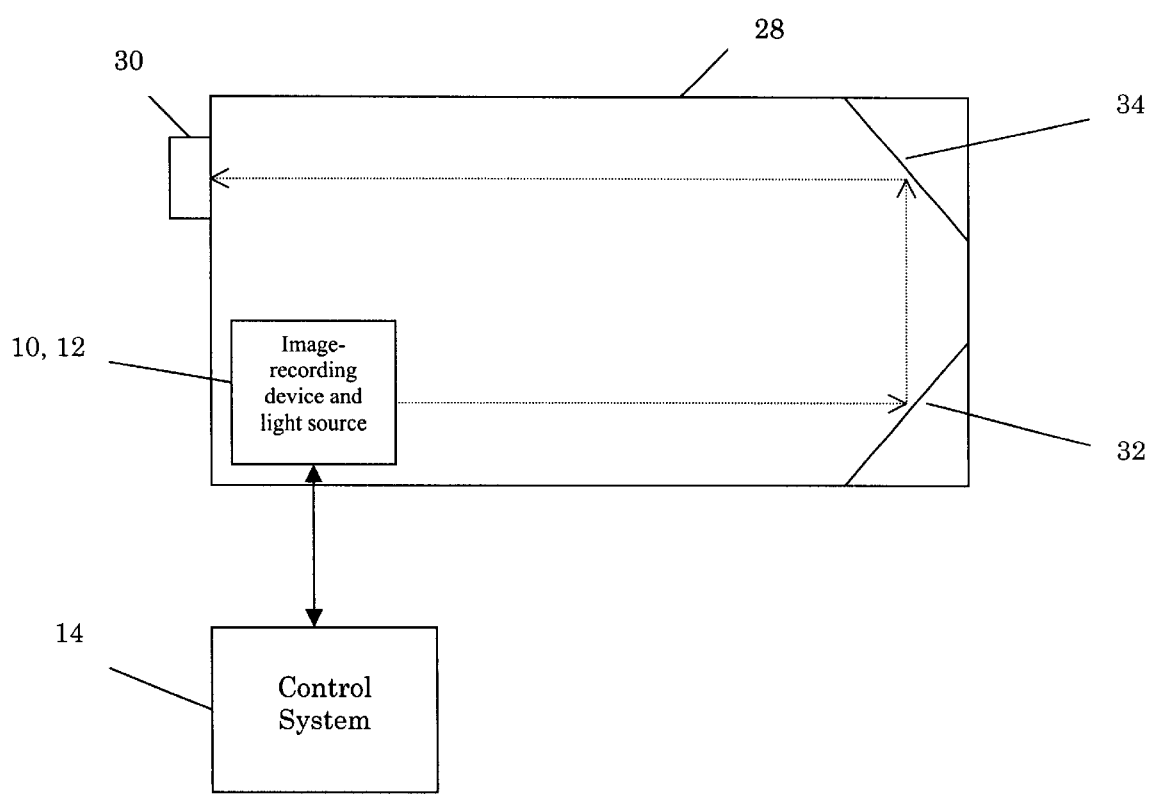
FIG. 16 is a drawing of a third embodiment of the present invention.

Referring to FIG. 16, one embodiment of the present invention further includes an enclosure 28 designed to hold the image-recording device 10 and the light source 12. The enclosure 28, as shown in FIG. 16, includes an opening (not shown), a headrest 30 positioned adjacent to the opening, a first mirror 32 positioned at a 45 degree angle with respect to the headrest 30, and a second mirror 34 positioned at a 45 degree angle with respect to the image-recording device 10 and light source 12. In this embodiment, the infrared and visible light generated by the light source 12 is reflected from the first mirror 32 to the second mirror 34 and from the second mirror 34 through the opening in the enclosure and the headrest 30. Using the headrest 30, a patient's eyes may be positioned adjacent to the opening in the enclosure so that the eyes are illuminated by light passing out of the enclosure 28.

Although this embodiment includes a pair of mirrors positioned at 45-degree angles, other embodiments might exclude these mirrors. In such an embodiment, the image-recording device 10 and light source 12 would be positioned at one end of the enclosure, and the opening in the enclosure and the headrest would be positioned at the opposite end of the enclosure. By using mirrors, however, it is possible to use a smaller length enclosure and still maintain an optical path that is actually longer than the length of the enclosure.

Thus, although there have been described particular embodiments of the present invention of a new and useful Sequential Eye Screening Method and Apparatus, it is not intended that such references be construed as limitations upon the scope of this invention except as set forth in the following claims.

The invention claimed is:

1. An apparatus for detecting eye abnormalities, comprising:
   a light source for sequentially illuminating two different meridians of the eyes in a time period shorter than a response time of the eyes; and
   an image-recording device for recording images of the eyes while each meridian of the eyes is illuminated by the light source.

2. The apparatus of claim 1, wherein the image-recording device comprises a digital camera having an optical axis.

3. The apparatus of claim 2, wherein the light source comprises at least two flashes positioned in different meridians of the optical axis of the digital camera.

4. The apparatus of claim 1, wherein:
   the light source includes an infrared light source for illuminating the eyes with infrared light; and
   the image-recording device is operable to record images of the eyes while illuminated with infrared light.

5. The apparatus of claim 4, further comprising a control system for causing the infrared light source to illuminate the eyes and for causing the image recording device to record images of the eyes while illuminated by infrared light.

6. The apparatus of claim 5, wherein the control system is further operable to analyze the infrared images to determine pupil size.

7. The apparatus of claim 6, wherein the control system is further operable to analyze the infrared images to identify non-refractive errors in the eyes.

8. The apparatus of claim 1, further comprising a control system for causing the light source to sequentially illuminate the eyes in at least two different meridians of the eyes and causing the image recording device to record images of the eyes while each meridian is illuminated.

9. The apparatus of claim 8, wherein the control system is further operable to analyze the images of the eyes to detect refractive errors in the eyes.

10. A method for identifying abnormalities in eyes, comprising the steps of:
    sequentially illuminating at least two different meridians of the eyes in a time period shorter than a response time of the eyes; and
    recording images of the eyes while each meridian is illuminated.

11. The method of claim 10, further comprising the steps of:
    illuminating the eyes with infrared light;
    recording an infrared image of the eyes while illuminated by the infrared light; and
    identifying non-refractive errors, in the eyes using the recorded infrared image.

12. The method of claim 11, further comprising the step of analyzing the infrared image to identify physical characteristics of the eyes.

13. The method of claim 12, wherein the step of identifying physical characteristics includes the step of identifying pupil size.

14. The method of claim 12, wherein the step of identifying physical characteristics includes the step of identifying gaze angle.

15. The method of claim 10, further comprising the step of analyzing the images to identify refractive errors in the eyes.

16. An apparatus for generating images of eyes for use in identifying non-refractive and refractive errors, comprising:
    a camera having an objective lens;
    an infrared light source located coaxially with the objective lens;
    a first flash positioned adjacent to the infrared light source and operable to emit light from a first meridian around the objective lens;
    a second flash positioned adjacent to the infrared light source and operable to emit visible light from a second meridian around the objective lens; and
    wherein the first and second flashes sequentially emit light from the first and second meridians around the objective lens in a time period shorter than a response time of the eyes.

17. The apparatus of claim 16, wherein the camera includes a color digital camera.

18. The apparatus of claim 16, wherein the camera includes a conventional film camera.

19. The apparatus of claim 16, wherein the infrared light source includes a plurality of infrared LEDS.

20. The apparatus of claim 16, wherein the first flash is positioned approximately 90 degrees from the second flash.

21. A system for generating infrared and visible images of eyes, comprising:
   a camera having an objective lens;
   an infrared light source located coaxially with the objective lens;
   a first flash positioned adjacent to the infrared light source and operable to emit light from a first meridian around the objective lens;
   a second flash positioned adjacent to the infrared light source and operable to emit visible light from a second meridian around the objective lens; and
   a control system, in communication with the camera, infrared light source, and flashes, operable to cause the infrared light source to emit infrared light and to cause the camera to capture an infrared image of the eyes using the emitted infrared light, the control system further operable to cause the flashes to fire sequentially in a time period shorter than a response time of the eyes and to cause the camera to capture an image of the eyes using the light emitted by the flashes.

22. The system of claim 21, wherein the camera includes a color digital camera.

23. The system of claim 21, wherein the camera includes a conventional film camera.

24. The system of claim 21, wherein the infrared light source comprises a plurality of infrared LEDs.

25. The system of claim 21, wherein the first flash is positioned approximately 90 degrees from the second flash.

26. The system of claim 21, wherein the control system includes a computer system having a monitor for displaying the infrared and sequential images of the eyes.

27. A system for identifying non-refractive and refractive errors in eyes, comprising:
   a camera having an objective lens;
   an infrared light source located coaxially with the objective lens;
   a first flash positioned adjacent to the infrared light source and operable to emit light from a first meridian around the objective lens;
   a second flash positioned adjacent to the infrared light source and operable to emit visible light from a second meridian around the objective lens;
   wherein the first and second flashes sequentially emit light from the first and second meridians around the objective lens in a time period shorter than a response time of the eyes; and
   a control system, in communication with the camera, infrared light source, and flashes, operable to cause the camera to record an infrared image of the eyes while illuminated by infrared light and sequential images of the eyes while illuminated by the flashes, the control system further operable to process the infrared image to identify non-refractive errors in the eyes and to process the sequential images to identify refractive errors in the eyes.

28. The system of claim 27, wherein:
   the non-refractive errors include media opacities or strabismus; and
   the refractive errors include myopia, hyperopia, or astigmatism.

29. The system of claim 28, wherein the control system identifies media opacities based on an amount of infrared light reflected by the pupil of the eye.

30. The system of claim 28, wherein the control system identifies strabismus by calculating a gaze angle of the eye using the infrared image.

31. The system of claim 27, wherein the control system calculates pupil diameter of the eyes using the infrared image.

32. The system of claim 27, wherein the control system identifies refractive errors by measuring an amount and distribution of light reflected by the pupil of the eye.

33. A method for identifying errors in eyes, comprising the steps of:
   generating an infrared image of the eyes;
   identifying non-refractive errors using the infrared image;
   generating sequential images of the eyes in a time period shorter than a response time of the eyes; and
   identifying refractive errors using the sequential images.

34. The method of claim 33, further including the step of determining pupil diameter.

35. The method of claim 33, wherein the step of identifying non-refractive errors includes the step of identifying media opacities or strabismus.

36. The method of claim 35, wherein the step of identifying media opacities includes the steps of measuring a mean amount of infrared light reflected by the pupil of the eye and comparing the mean amount to an actual amount reflected by the pupil of the eye on a pixel by pixel basis.

37. The method of claim 35, wherein the step of identifying strabismus includes the step of measuring eye gaze angle.

38. The method of claim 33, wherein the step of identifying refractive errors includes the step of identifying myopia, hyperopia, or astigmatism.

39. The method of claim 38, wherein the step of identifying myopia, hyperopia, or astigmatism includes the step of measuring a distribution of light reflected by the pupil of the eye on each sequential image.

40. The method of claim 38, wherein the step of identifying myopia, hyperopia, or astigmatism includes the step of defining a line through each pupil of the eye, calculating the slope of each line, and comparing the slopes of each line.

* * * * *